United States Patent [19]

Lin et al.

[11] Patent Number: 4,537,909

[45] Date of Patent: Aug. 27, 1985

[54] ALCOHOL SYNTHESIS

[75] Inventors: Fan-Nan Lin; Filippo Pennella, both of Bartlesville, Okla.

[73] Assignee: Phillips Petroleum Company, Bartlesville, Okla.

[21] Appl. No.: 584,374

[22] Filed: Feb. 28, 1984

[51] Int. Cl.³ .................. C07C 27/06; C07C 29/15
[52] U.S. Cl. .................................................. 518/713
[58] Field of Search ........................................ 518/713

[56] References Cited

U.S. PATENT DOCUMENTS 4,122,110 10/1978 Sugier et al. .................. 260/449.5
4,291,126 9/1981 Sugier et al. ...................... 518/713
4,459,369 7/1984 Passariello ......................... 518/713

OTHER PUBLICATIONS

M. Ichikawa, "Catalysis by Supported Metal Crystallites from Carbonyl Clusters, II., Catalytic Ethanol Synthesis from CO and $H_2$ under Atmospheric Pressure over Supported Rhodium Crystallites Prepared from Rh Carbonyl Clusters Deposited on $TiO_2$, $ZrO_2$ and $La_2O_3$", Bulletin of the Chemical Society of Japan, vol. 51 (8), pp. 2273–2277 (1978).

Primary Examiner—Howard T. Mars
Attorney, Agent, or Firm—Howard D. Doescher

[57] ABSTRACT

The preparation of alcohols from synthesis gas has been beneficiated by the use of a novel five-component catalyst system comprising an iron group metal and an activity improving amount of a precious metal such as rhodium.

8 Claims, No Drawings

ALCOHOL SYNTHESIS

This invention relates to a catalyst and a process utilizing the catalyst for the production of alcohols from carbon monoxide and hydrogen. In accordance with one aspect, this invention relates to an iron group metal-containing catalyst promoted with a precious metal. In accordance with another aspect, this invention relates to an improved process for the production of alcohols from synthesis gas utilizing a precious metal promoted iron group metal-containing catalyst exhibiting higher catalyst activity and reduced deactivation during use than unpromoted catalyst.

BACKGROUND

The Fischer-Tropsch process for the production of straight chain hydrocarbons and oxygenated derivatives thereof from synthesis gas (CO and $H_2$) is well known. Such reactions generally suffer from the drawback that selectivities to specific products and catalyst activity are low.

In the synthesis of alcohols from CO and $H_2$, catalysts containing metals of the iron group give rise to the formation of linear higher alcohols, i.e., alcohols other than methanol. Cobalt-containing catalysts in particular lead to the formation of large amounts of ethanol. Some of the previous metals of Group VIII, e.g., rhodium, also promote the formation of ethanol. The present invention is directed to an improved catalyst containing an iron group metal and a precious metal which exhibits increased catalyst activity without substantially affecting alcohol product distribution.

OBJECTS OF THE INVENTION

It is an object of the invention to produce alcohols from synthesis gas more efficiently.

It is a further object of the invention to provide a catalyst for the preparation of $C_2+$ alcohols from synthesis gas.

It is a further object to provide a process for the preparation of higher alcohols from synthesis gas via catalytic synthesis.

INVENTION

It has been discovered that the synthesis of alcohols, especially those containing one or more carbon atoms, from synthesis gas can be effectively carried out in the presence of a five-component catalyst system.

In accordance with the invention, it has been found that the addition of a small amount of a precious metal, such as rhodium, to an iron group metal-containing catalyst, such as cobalt, significantly increases the overall alcohol yield from a synthesis gas without an increase in the methanol fraction. In addition, the precious metal promoted catalyst deactivated more slowly than an unpromoted catalyst.

In one embodiment, linear higher alcohols are produced from synthesis gas over a catalyst comprising (a) copper, (b) cobalt, (c) at least one element selected from chromium, iron, vanadium, and manganese and (d) at least one alkali metal, with the concomitant use of a small concentration of rhodium, e.g., about 0.5 weight percent, based on total catalyst composition, which addition increases catalyst activity without significantly changing selectivity.

ADVANTAGES

The catalyst composition and process of the invention have several advantages over those of the prior art. Principally, use of the instant catalyst results in an increase in higher alcohol yield without an increase in the production of methanol. In addition, the novel catalyst system has increased activity and life when compared to prior art catalyst for the same syntheses.

Other advantages and aspects of the invention will become apparent from a consideration of the following description.

DETAILED DESCRIPTION OF THE INVENTION

The production of saturated alcohols from synthesis gas is a well known technology. U.S. Pat. No. 4,122,110, the disclosure of which is hereby incorporated by reference, describes one useful catalyst system containing an iron group metal for the synthesis of such alcohols.

THE CATALYST COMPOSITION

The catalyst compositions used herein contain, as essential components:
 (a) a copper component,
 (b) an iron group component,
 (c) a component of element numbers 23–26,
 (d) an alkaline metal component, and
 (e) a precious metal, such as a rhodium component.

Other ingredients or additives can be present so long as their presence does not deleteriously affect the cooperative function of these five essential ingredients.

After calcination, the metal components will generally be present as oxides or other suitable species conventionally employed in analogous synthesis. Heat-decomposible salts or other compounds or substances containing these metals can be used in preparing the catalysts of the invention.

Component (a) will be at least one of copper or a copper-containing substance having requisite compatibility with the other four components. Example compounds used in preparing the catalyst include copper(II)nitrate and copper(II)acetate. The quantity of component (a) employed in the instant catalyst will be from about 15 percent to about 70 percent, preferably from about 20 percent to about 50 percent, based upon the weight of the total catalyst composition. Mixtures of copper components are operable.

The iron group metal component, i.e., component (b), is at least one element of atomic number 26 through 28 of the Periodic Table, i.e., iron, cobalt, and nickel. Cobalt is preferred. Useful cobalt-containing substances for use herein include water soluble salts such as cobalt(II)nitrate, cobalt(II)acetate, cobalt(II)oxalate, with nitrate preferred. The quantity of component (b) to be used in the instant catalyst will range from about 5 percent to about 50 percent with about 10 percent to about 40 percent, based on total catalyst weight, preferred, Mixtures of (b) components are contemplated.

Component (c) comprises at least one element other than component (b) selected from the group containing chromium, iron, vanadium, and manganese. Chromium-containing substances are preferred. Example compounds useful in preparing the catalyst include chromium(IV)oxide, chromium(III)nitrate, manganese(II)nitrate, and iron(II)nitrate. The quantity of component (c) will generally be within the range of about 5 percent to about 50 percent, preferably about 10 percent to about 40 percent, based on total catalyst weight.

Component (d) of the catalyst is one or more alkali metal-containing substances. Useful substances include sodium hydroxide, potassium hydroxide, and the like. The quantity of this fourth component in the inventive catalyst will generally range from about 0.1 percent to about 10 percent, with quantities of about 0.5 percent to about 5 percent preferred. Potassium-containing substances are highly preferred.

The last required ingredient, component (e), contains at least one rhodium-containing substance. Generally, operative rhodium substances include metallic rhodium, and rhodium(II)nitrate. Mixtures of rhodium-containing components are operable. The quantity of the rhodium-containing component in the total catalyst composition will generally be sufficient to increase the catalyst activity and catalyst life without significantly changing selectivity. Generally, the small promoting amount will be greater than about 0.1 weight percent. That is, quantities of about 0.1 percent to about 5 percent, with about 0.2 percent to about 3 percent being preferred, based upon total catalyst weight.

Inert support materials, such as alumina or silica, can be combined with the catalyst to provide increased catalyst surface area or increased catalyst crush strength. Up to 50 weight percent, but preferably less than 20 weight percent, of the finished catalyst can be composed of inert support material.

The catalyst components are brought together via suitable physical and/or chemical processing techniques. Generally, component (e) will be added via impregnation.

The sequence of combination of the five components employed herein is important. Generally, the (a), (b) and (c) components will be combined prior to addition of the (d) and (e) components. It is preferred that component (e) be brought into combination last.

REACTANTS

The synthesis gas employed as the principal reactant in the inventive process contain chiefly hydrogen and carbon monoxide. Generally, operable reactants will contain about 35 to about 95 volume percent hydrogen, about 5 to about 35 volume percent carbon monoxide, about 0 to about 30 percent carbon dioxide, and about 0 to about 10 percent nitrogen. Preferred reactants will have the following composition by volume:

$H_2:CO = 66.34$.

It should be understood that the combination of chemical species present in the reactive synthesis gas will not total more than 100 percent by volume.

The synthesis gases used herein include commercially available ones.

REACTION CONDITIONS

Typical conditions to be employed in the synthesis reactions of the invention are well known. The following are merely suggested parameters from which the skilled artisan can extrapolate. Suitable temperatures are about 200° C. to about 350° C., with about 250°–300° C. preferred. Suitable pressures include about 300 to about 3000 psi, with about 500–1500 psi preferred. Other reaction variables such as gas flow rate and catalyst volume may be selected in accordance with the particular reactants and reaction vessel involved.

PRODUCTS

The principal products derived via the reaction of the instant process are straight chain alcohols. Generally, the chemical species produced will be saturated alcohols containing from about 1 to about 10 carbon atoms. Often, chemical species containing $C_{1-5}$ alcohols will comprise about 90 percent or more of the reaction product.

In addition to methanol, highly desirable higher alcohols, such as ethanol, n-butanol, and n-pentanol are produced via the instant process. Due to the relative complexity of procedures for separation of methanol, it is desirable that the selectivity of $C_{2+}$ alcohols be maintained at acceptably high levels. Operating within the teachings of this invention, selectivities to alcohols containing two carbons or more will generally be above 30 percent. Values of 50 percent to 70 percent are not uncommon.

EXAMPLES

Preparation of the catalyst of this invention and its use to synthesize alcohols is illustrated in the following examples.

EXAMPLE I

The preparation of Catalyst $B_1$ in U.S. Pat. No. 4,122,110, Col. 3, provided the basis for preparing the catalyst of this invention. The following compounds were combined: 16 g (0.160 moles) of $CrO_3$, 48 g (0.199 moles) of $Cu(NO_3)_2.3H_2O$, 58.2 g (0.200 moles) of $Co(NO_3)_2.6H_2$, and 10 g (0.052 moles) of citric acid. They were dissolved, with stirring, in 45 mL of water, dried by heating with stirring for two hours at about 200° C. on a hot plate in air. Finally the catalysts were calcined in air for three hours at 450° C. The calcined product weighed 42.05 grams. It was treated with a solution of 1.00 g KOH dissolved in 70 mL water and 40 mL methanol. Solvent was partially removed by drying in a microwave oven under nitrogen, but drying was completed under an infrared heating lamp with the sample exposed to air. This is Catalyst A.

To 8.05 g of catalyst A was added a solution containing 0.072 g $Rh(NO_3)_2.2H_2O$ (=0.0114 g Rh) dissolved in 9 mL of water to impregnate it. Solvent was removed by evaporation and the remaining catalyst was calcined in air for 2.4 hours at 200° C. followed by 3.6 hours at 400° C. This is Catalyst B.

EXAMPLE II

Catalysts A and B were used in runs to produce alcohols by selective hydrogenation of carbon monoxide. The runs were made using 5 mL of catalyst, diluted with 25 mL of 3 mm glass beads, placed in a 1" pipe stainless steel reactor mounted vertically in a controlled temperature furnace. Synthesis gas having the composition 65 percent $H_2$, 20 percent CO, 13 percent $CO_2$, 2 percent $N_2$ (all expressed as volume percent) passed downflow at 8000 GHSV and 950 psig pressure through the reactor, leaving via a trap cooled to 0° C. and at the pressure of the process. Arrangement of the trap was such that it could be isolated and removed from the system for weighing to determine the quantity of liquid that it contained. The liquid was sampled for analysis by gas liquid chromatography. Table I summarized pertinent information of runs made with catalysts A and B. Weight of liquid product collected after one and two hours on stream is recorded.

TABLE I

| Catalyst | A | B |
| --- | --- | --- |
| Wt. 5 mL catalyst, g | 3.17 | 3.62 |
| Wt. product, first hour, g | 0.92 | 1.94 |
| Wt. product, second hour, g | 0.60 | 1.04 |

Table II summarizes the analytically measured yields of water and alcohols and the calculated selectivity to alcohols on a water-free basis.

TABLE II

| | Catalyst A | | Catalyst B | |
| --- | --- | --- | --- | --- |
| | Yield, wt % | Selectivity mole % | Yield, wt % | Selectivity mole % |
| $H_2O$ | 88.7 | — | 88.0 | — |
| $CH_3OH$ | 3.16 | 38.5 | 3.17 | 37.0 |
| $C_2H_5OH$ | 5.05 | 43.2 | 5.28 | 43.2 |
| $C_3H_7OH$ | 1.77 | 11.6 | 2.04 | 12.7 |
| $C_4H_9OH$ | 0.97 | 5.2 | 1.06 | 5.4 |
| $C_5H_{11}OH$ | 0.36 | 1.5 | 0.43 | 1.7 |

The compositions of the alcohol mixtures synthesized by each catalyst are considered to be essentially the same. However, as shown in Table I, inventive catalyst B was appreciably more active than Catalyst A. During the first and second hours 0.54 and 0.29 g liquid/g catalyst-hour, respectively, were produced. In contrast, catalyst A which did not contain rhodium produced 0.29 and 0.19 g liquid/g catalyst-hour, respectively.

Reasonable variations, such as those which would occur to a skilled artisan, may be made herein without departing from the scope of the invention.

We claim:

1. A process for the production of alcohols from synthesis gas which comprises contacting a synthesis gas under suitable reaction conditions with a catalyst consisting of:
   (a) at least one copper component,
   (b) at least one iron group metal component,
   (c) at least one metal component other than compounds (b) having a Periodic element number of 23 to 26,
   (d) at least one alkali metal component, and
   (e) a promoting amount of about 0.1 to about 5 weight percent of at least one rhodium component, which promoting amount is a small effective amount sufficient to increase catalyst activity and catalyst life without significantly changing selectivity in comparison with the unpromoted catalyst.

2. A process for preparing alcohols from synthesis gas according to claim 1 wherein (b) is cobalt.

3. A process for preparing alcohols from synthesis gas according to claim 1 wherein (c) is chromium, iron, vanadium, or manganese.

4. A process according to claim 1 wherein carbon dioxide is also present in the synthesis gas.

5. A process according to claim 1 wherein the catalyst contains copper, cobalt, chromium, potassium, and rhodium.

6. A process according to claim 5 wherein the synthesis gas feed comprises hydrogen, carbon monoxide, carbon dioxide and nitrogen.

7. A process according to claim 1 wherein the reaction temperature ranges from about 200° to about 350° C. and the reaction pressure ranges from about 300 to about 3,000 psi.

8. A process for preparing alcohols from synthesis gas comprising the step of contacting synthesis gas feed with a catalyst consisting of the following elements:
   (a) about 15 to about 70 weight percent copper,
   (b) about 5 to about 50 weight percent cobalt,
   (c) about 5 to about 50 weight percent of at least one element selected from chromium, iron, vanadium, and manganese,
   (d) about 0.1 to about 10 weight percent of an alkali metal, and
   (e) about 0.1 to about 5 weight percent rhodium.

* * * * *